United States Patent [19]

Li

[11] 4,300,005

[45] Nov. 10, 1981

[54] PREPARATION OF VINYL CHLORIDE

[75] Inventor: Tao P. Li, Chesterfield, Mo.

[73] Assignee: Monsanto Co., St. Louis, Mo.

[21] Appl. No.: 856,889

[22] Filed: Dec. 2, 1977

[51] Int. Cl.[3] ....... C07C 17/10

[52] U.S. Cl. ....... 570/224

[58] Field of Search ....... 260/656 R, 654 A; 570/224

[56] References Cited

U.S. PATENT DOCUMENTS

| | | | |
|---|---|---|---|
| 3,217,064 | 11/1965 | McGreevy et al. | 260/656 R |
| 3,308,184 | 3/1967 | Bajars | 260/680 D |
| 3,308,198 | 3/1967 | Bajars | 260/680 D |
| 3,359,343 | 12/1967 | Bajars | 260/680 D |
| 3,427,359 | 2/1969 | Rectenwald et al. | 260/656 R |
| 4,042,639 | 8/1977 | Gordon et al. | 260/656 R |

FOREIGN PATENT DOCUMENTS

| | | | |
|---|---|---|---|
| 1039369 | 8/1966 | United Kingdom | 260/656 R |

*Primary Examiner*—Delbert E. Gantz
*Assistant Examiner*—Joseph A. Boska

[57] ABSTRACT

Monohalogenated olefins are selectively prepared in high yields from alkanes having 2 to 4 carbon atoms by the reaction of such hydrocarbons with a hydrogen halide and a source of oxygen at a temperature from about 400° to about 650° C. in contact with a catalyst comprising a copper halide and an alkali metal phosphate, particularly potassium phosphate, deposited on an inorganic support. Typically, vinyl chloride is prepared in one step from ethane.

10 Claims, No Drawings

PREPARATION OF VINYL CHLORIDE

BACKGROUND OF THE INVENTION

The present application relates to the conversion of alkanes to unsaturated halogenated products such as vinyl halides. More particularly, it relates to the conversion of ethane directly to vinyl chloride in high yields by the oxychlorination reaction utilizing a novel highly selective catalyst.

The conversion of hydrocarbons to useful halogenated hydrocarbons by the so-called "oxychlorination" reaction, i.e., the reaction of the hydrocarbon, a hydrogen halide as the source of the halogen and a source of elemental oxygen, in the presence of copper-containing catalysts is well known in the art. It is known, for example, to react ethane with hydrogen chloride and oxygen in contact with catalysts which include copper oxides, copper chlorides, copper oxychlorides, copper silicates and the like to produce chlorinated hydrocarbons such as vinyl chloride, ethyl chloride, ethylene dichloride and the like. The yields of any desired specific chlorinated products, however, have been generally poor which has led to a search for active catalysts to give cleaner or more selective reactions. One such catalyst is described in U.S. Pat. No. 3,173,962. This patent teaches the oxychlorination of an alkane having from 2 to 6 carbon atoms and preferably ethane in the presence of an iron phosphate preferably supported on an inert carrier such as silica, for example. Other metallic cations such as nickel, cobalt, copper, chromium, tin, lead, cerium, manganese, bismuth, magnesium, cadmium, vanadium and generally metals of Groups I through IV of the Periodic Table are disclosed as useful in conjunction with iron. The products obtained with this catalyst are predominantly ethylene, ethyl chloride and sometimes 1,2-dichloroethane (DCE), also called ethylene dichloride.

In another patent, No. Br. 1,039,369, the conversion of ethane to vinyl chloride by oxychlorination in the presence of water is disclosed using as catalysts inorganic oxygen-containing compounds such as simple oxides and oxychlorides of multivalent metals such as iron, cerium, manganese, uranium, vanadium, nickel, chromium and cobalt together with promoters which are inorganic compounds of Li, Na, K, Pb, Ce, Ca, Mg, Sr, Ba, Zn, Cd, B, In, P and Tl, The catalysts can be initially introduced in the form of oxygenated compounds such as carbonates, nitrates, phosphates and hydroxides and thus it is disclosed inorganic compounds resulting from this form of introduction may also be present in the reaction zone. Even with the preferred iron-containing catalysts, and steam as a reactant, however, the selectivity of conversion of ethane to vinyl chloride in a single-step reaction does not generally average 50%.

Other catalytic compositions disclosed as useful for converting ethane directly to vinyl chloride are described in U.S. Pat. Nos. 3,420,901 and 3,557,229. In the former patent, a complex copper-alumina catalyst is employed in the oxychlorination reaction but there is no indication of the effectiveness of the catalyst for producing vinyl chloride from ethane. There are no examples directed to the use of ethane as a reactant to support the bare disclosure. In the latter patent, a catalyst melt formed from a chloride of a multivalent metal, such as copper chloride, is employed but only 37% of the ethane converted goes to the production of chlorinated hydrocarbons including vinyl chloride which constituted only 18.8% of the chlorinated products mixture.

It is evident from the foregoing consideration of the prior art, that the known processes for producing vinyl chloride from ethane in one step suffer from the obvious disadvantage that the known catalysts for the reaction are not highly selective. It is, accordingly, an object of the present invention to provide an oxychlorination process utilizing a novel catalyst to produce vinyl chloride in high yields in one step from ethane. This and other objects and advantages of the invention will become more readily apparent from the following detailed description of the invention.

SUMMARY OF THE INVENTION

According to the present invention, monohalogenated olefins are selectively prepared in high yields by reacting an alkaline having 2 to 4 carbon atoms with a hydrogen halide and a source of oxygen at a temperature in the range from about 400° C. to about 650° C. in contact with a catalyst system comprising a copper halide and an alkali metal phosphate deposited or carried on an inorganic support. More particularly, the present invention is directed to the production of vinyl chloride by the oxychlorination of ethane at a temperature from about 500° C. to about 600° C. in contact with a catalyst comprising copper chloride and potassium phosphate. The catalyst may contain other components such as halides of the platinum-group metals, e.g., platinum itself, palladium, ruthenium, rhodium, iridium and the like, and the halides of the metals of Groups I and II of the periodic system.

DESCRIPTION OF THE PREFERRED EMBODIMENTS

The catalyst employed in the process of the invention is readily prepared by admixing of the support material or carrier with a solution of the copper halide or of the copper halide and any other metal halides which are to be included in the catalyst composition in the proper amount in water or, preferably, in an alcohol. After thorough mixing, the solids are separated from the mixture or slurry either mechanically and/or by evaporation of the solvent and then subjected to drying at a temperature from about 100° C. to about 200° C. for a period of from about one to about ten hours. The solid remaining is converted into any desired form by grinding, pelletizing, etc., after which it is heat-treated while under fluidization conditions with air at a temperature from about 300° to about 600° C. for a period from about 2 to about 8 hours and preferably at a temperature of about 450° C. for about 3 to about 6 hours.

The heat-treated material is then contacted with an aqueous solution in the desired concentration of the alkali metal phosphate, dried and again heat-treated under conditions substantially the same as those described above to obtain the finished catalyst. Alternatively, the alkali metal phosphate can be incorporated by adding it to the dried copper-containing solid before the initial heat treatment is carried out.

Where more than two metal compounds are used in the catalyst composition, the compounds of the metals other than copper can be deposited on the support as described above. The resulting solid is then mixed with anhydrous cupric chloride and again heat-treated with air at 450° C. for 6 hours to provide the finished catalyst. When alkali metal compounds such as sodium and potassium chlorides, for example, are used in the catalyst composition, these are placed on the support first using the usual impregnation, drying and calcining technique because they tend to precipitate platinum and sometimes copper from the solution.

Various materials may serve as suitable supports for the catalyst of the present invention. Among the many which can be used may be mentioned alumina, silica gel, silica-alumina, silica-magnesia, bauxite, magnesia, silicon carbide, titania, zirconium silicate and the like. The preferred support is alumina. The surface area of the support may range up to 150 $m^2/g$ but catalyst supports having a low surface area, i.e., $<30$ $m^2/g$ are preferred and those of $<10$ $m^2/g$ are even more preferred. Available support materials of high surface area may be readily calcined to reduce their surface area to the desired level.

The concentration of copper on the support may vary from about 0.1 to about 10% by weight and preferably is from about 1 to about 5% by weight. The concentration of alkali metal as the phosphate is from about 1% by wt. to about 10% by wt. and preferably is from about 3 to about 6% by weight. Compounds of so-called platinum-group metals can also be incorporated in the catalyst composition. These are compounds of such metals as platinum, palladium, rhodium, ruthenium, osmium, and iridium, particularly the halide of these metals, which may have a beneficial effect on the reaction. When a platinum-group metal is employed with the copper, the concentration of this metal is generally in the range from about 0.1% by weight to about 1% by weight and preferably is about 0.5% by weight. Alkali metal halides may also be incorporated if desired in the catalyst composition. The amounts of the latter if they are used will generally vary between about 0.5 to about 5.0% by weight.

The present process is particularly applicable to the manufacture of monochlorinated and monobrominated substituted olefins such as vinyl chloride and vinyl bromide from ethane. However, other alkanes such as propane and butane can be oxychlorinated employing the catalyst of the invention to produce the corresponding monohalogenated olefins.

The hydrogen halide employed is that corresponding to the desired monohalogenated olefin to be produced. Thus, when vinyl chloride is produced according to the invention, hydrogen chloride is employed as the hydrogen halide while for vinyl bromide as a product, hydrogen bromide is employed.

Elemental oxygen may be used or any oxygen-containing gas stream such as air. Gaseous inert diluents such as nitrogen, helium, carbon dioxide and the like or excess ethane or excess hydrogen chloride may also be present but are not necessary.

The relative molar proportions of alkane, hydrogen halide and oxygen may vary from 0.25 to 3.0 moles of oxygen per mole of alkane and from 0.5 to 5 moles of hydrogen halide per mole of alkane. Preferred molar ratios include 0.5–1.5 mole of oxygen and 0.5 to 2 moles of hydrogen halide per mole of alkane.

Generally, the reaction is conducted at a temperature from about 400° C. to about 650° C. but preferably reaction temperatures are maintained in the range from about 500°–600° C. Suitable pressures are those in the range from atmospheric to about 100 psig. Preferably, pressure is maintained at approximately atmospheric.

The process may be conducted using either a fixed bed, moving bed or fluidized bed of catalyst but the use of the fluidized bed technique is preferred. The reactants may be charged to the bottom of the reactor containing the catalyst in a finely divided state thus serving to fluidize the catalyst. The three reactants may be introduced into the reactor in separate streams or the air or oxygen may be introduced into a mixture of the alkane and hydrogen halide. Because of the explosive limits of the various hydrocarbon feeds, care should be taken not to allow a mixture of alkane and oxygen to reach reaction temperature in the absence of the hydrogen halide. The minimum gas velocity for fluidizing the catalyst is low. Linear gas velocities of the order of 0.1 to 0.5 foot per second are generally satisfactory and avoid excessive carryover of catalyst fines. The depth of the catalyst bed should be such as to permit a satisfactory fluidized condition of the catalyst to be achieved and to provide sufficient contact time for substantial conversion to the desired product at the temperature employed. A superficial contact time of 0.1 to 10 seconds or more is sufficient under the usual operating conditions with a preferred contact time being in the range from about 1 to about 5 seconds.

The invention is illustrated in the following examples which are not, however, to be construed as limiting the scope thereof in any manner except as it is limited in the attached claims. Conversions and yields given in the tables are defined as follows:

$$\% \text{ Conversion} = \frac{\text{HCl reacted}}{\text{HCl in feed}} \times 100$$

$$\% \text{ Yield on } x = \frac{x \text{ converted to product}}{x \text{ reacted}} \times 100$$

$$\text{where } x = C_2H_6 \text{ or HCl}$$

EXAMPLE 1

A catalyst containing 3.0% copper, 0.5% lithium, 0.5% platinum and 3% potassium as potassium phosphate supported on alumina and having a surface area of 7.6 $m^2/g$ was prepared as follows. To a solution of 0.5494 g of the hexahydrate of hydrochloroplatinic acid ($H_2PtCl_6.6H_2O$), 1.2241 g of lithium chloride (LiCl) and 2.5614 g of copper chloride ($CuCl_2$) in 50 ml of methanol there was added with thorough mixing 40 g of alumina known by the tradename "Alcoa F-1" which had been calcined at 1100° C. to provide a surface area of 9.4 $m^2/g$. The resulting mixture was subjected to evaporation and dried at 110° C. for about 2 hours. It was then transferred to a fluidized bed reactor and fluidized with nitrogen at 400° C. for 6 hours. After the heat-treatment the solid material was added to a solution of 2.1683 g of $K_3PO_4$ in 30 ml of $H_2O$ and mixed thoroughly. The liquid was evaporated from the mixture after which it was fluidized with air at 400° C. for three hours.

The above-described catalyst was employed in a fluidized bed for the reaction between ethane, hydrogen chloride and air. The reaction was carried out in a pyrex reactor, one inch in diameter and 24 inches long equipped with rotameters for measuring gas flow, flow regulators and pressure controllers. The reactor was equipped with Nichrome heating tape and asbestos insulation. Reactor temperature was measured by means of thermocouples located at five different points in the thermowell from the bottom to the top of the reactor. The gaseous reactants were introduced at a rate sufficient to fluidize the catalyst. Catalyst fines carried out by the reaction effluent leaving the top of the reactor were accumulated in a collector heated by an electric tape to a temperature from 140° to 150° C. to prevent condensation to liquid product. The effluent gases were then passed through suitable condensers and water and liquid product were collected in suitable receivers. Off-gas was sent through a hydrogen chloride scrubber and then vented. Unreacted HCl was collected in water and titrated using a standard alkali solution. Product composition was determined by gas chromatographic analysis of an off-gas sample taken from a sampling valve located ahead of the HCl scrubber. Results of two runs at a contact time of 1.0 second, two different reactant mole ratios and a temperature of 550° C. are presented in Table 1 below showing the two major products of the reaction, vinyl chloride (VCM) and ethyl chloride (EtCl). Minor amounts of other chlorinated hydrocarbons such as tetrachloroethylene, trichloroethylene, 1,1- and 1,2-dichloroethane, chloroform, and other saturated and unsaturated halohydrocarbons were also identified in the product.

TABLE 1

| Run No. | 1 | 2 |
|---|---|---|
| $C_2H_6$/HCl/air, mol | 1/1/4.76 | 1/1/7.15 |
| HCl Conversion, % | 62.8 | 77.5 |
| VCM Yield, mol % | | |
| on $C_2H_6$ | 77.1 | 76.9 |
| on HCl | 62.7 | 60.3 |
| EtCl Yield, mol % | | |
| on $C_2H_6$ | 11.1 | 10.7 |
| on HCl | 9 | 8.4 |

It will be seen that the yields of vinyl chloride resulting from the use of this catalyst containing $K_3PO_4$ are significantly better than those obtained in the prior art for a single-step reaction. In addition the major by-product is ethyl chloride which can be subsequently oxydehydrogenated to vinyl chloride by simple recycle operations using the same catalyst employed herein as described in my copending application filed of even date herewith.

EXAMPLE 2

A copper chloride catalyst containing potassium phosphate was prepared as follows: About 710 g of the same alumina employed in Example 1 was calcined to reduce its surface area to below 10 $m^2/g$. The calcined alumina was placed in two Vycor dishes in a muffle furnace at 1200° C. for about 16 hours. The final surface area of the alumina was found to be about 3.1 $m^2/g$.

To the alumina there was added with stirring 45 g of $CuCl_2$ dissolved in 630 ml of methanol. The mixture was dried under fluidized bed conditions with air flow at room temperature until it became a free-flowing solid. The solid was dried at 110° C. overnight and then heat-treated at 450° C. while fluidized with air for about 6 hours. The dried material was cooled to room temperature and 115 g of $K_3PO_4$ dissolved in 200 ml of water was added to it. The resulting mixture after thorough mixing was dried in a fluidized bed at 450° C. The finished catalyst contained 3.0% copper and 9% potassium as $K_3PO_4$ and had a surface area of 1.2 $m^2/g$.

The catalyst prepared as described above was charged to the reactor described in Example 1. Ethane, HCl and air were introduced into the bottom of the reactor at rates to maintain the catalyst in a fluidized state and the reaction products were withdrawn from the top and treated as described in Example 1. Conditions of reaction and the results obtained are recorded in Table 2. The selectivity of the copper and potassium phosphate-containing catalyst is readily apparent from the high yields of vinyl chloride which can be obtained under the optimum conditions. As in Example 1, the other major product of the reaction is ethyl chloride which can be subsequently recycled to increase the vinyl chloride yield because the catalyst is also suitable for conversion of ethyl chloride to vinyl chloride by oxydehydrogenation.

TABLE 2

| Run No. | Temp. °C. | Contact Time, Sec. | $C_2H_6$/HCl/Air Moles | HCl Conv. % | VCM Yield (on $C_2H_6$) | EtCl Yield (on $C_2H_6$) | VCM Yield (on HCl) | EtCl Yield (on HCl) |
|---|---|---|---|---|---|---|---|---|
| 1 | 600 | 1.13 | 2/1/7.15 | 61.4 | 85.0 | 7.5 | 74.5 | 6.6 |
| 2 | 550 | 1.20 | " | 79.8 | 70.9 | 20.2 | 62.4 | 17.8 |
| 3 | 500 | 1.28 | " | 96.9 | 37.7 | 48.7 | 32.4 | 41.8 |
| 4 | 450 | 1.36 | " | 97.4 | 17.0 | 68.3 | 14.5 | 58.0 |
| 5 | 400 | 1.47 | " | 97.8 | 4.2 | 82.6 | 3.7 | 71.7 |
| 6 | 375 | 1.52 | " | 41.0 | 2.5 | 87.5 | 2.2 | 77.9 |
| 7 | 350 | 1.58 | " | 23.5 | 3.3 | 88.5 | 3 | 81 |
| 8 | 500 | 0.64 | " | 96.4 | 30 | 54.8 | 25.5 | 46.6 |
| 9 | 500 | 2.56 | " | 67.8 | 57.5 | 34.5 | 52.2 | 31.3 |
| 10 | 550 | 2.4 | " | 44.6 | 88 | 6.6 | 82.1 | 6.1 |
| 11 | 550 | 0.60 | " | 94.3 | 58.3 | 29.4 | 50.2 | 25.3 |
| 12 | 550 | 1.2 | 2/0.9/5 | 52.8 | 66.5 | 27.4 | 61.3 | 25.3 |
| 13 | 550 | 1.2 | 2/1/10 | 89.4 | 73.8 | 13 | 61.7 | 10.9 |
| 14 | 550 | 1.2 | 1/0.9/10 | 94.7 | 73.1 | 8.4 | 57.7 | 6.7 |
| 15 | 550 | 1.2 | 3/1/10 | 83.4 | 65.8 | 26.4 | 58.7 | 23.6 |
| 16 | 550 | 1.2 | 4/1/2 ($O_2$) | 76.8 | 54.8 | 38.2 | 49.8 | 34.7 |

EXAMPLE 3

An oxychlorination catalyst was prepared as follows. About 100 cc (41.89) of an inorganic support identified by the trade name "Celite" (Type V) having a particle size of 30–80 mesh and a surface area of 3.1 $m^2/g$ was impregnated with a solution of 5.3023 g of $CuCl_2$ in 70 ml of methanol. The mixture was subjected to evaporation, dried and then heat-treated during fluidization at 450° C. for 6 hours. To the resulting solid there was added a solution of 6.8124 g of $K_3PO_4$ in 70 ml of water. After drying, the material was heat-treated under fluidization conditions at 450° C. for 3 hours. The finished catalyst contained 6.0% copper and 9.0% potassium as $K_3PO_4$ and had a surface area of 1.7 $m^2/g$.

The catalyst prepared as described above was used to oxychlorinate ethane in the apparatus of Example 1 and following the procedure described in that example.

Conditions of reaction and the results obtained are presented in Table 3 below.

TABLE 3

| Run No. | Temp. °C. | Contact Time, Sec. | $C_2H_6$/HCl/Air Mole Ratio | HCl Conv. % | VCM Yield % (on $C_2H_6$) | VCM Yield % (on HCl) | EtCl Yield % (on $C_2H_6$) | EtCl Yield % (on HCl) | 1,2-DCE Yield % (on $C_2H_6$) | 1,2-DCE* Yield % (on HCl) |
|---|---|---|---|---|---|---|---|---|---|---|
| 1 | 500 | 1.92 | 2/1/7.15 | 95.7 | 37.9 | 34.5 | 54.6 | 49.7 | 2.5 | 4.5 |
| 2 | 550 | 1.80 | 2/1/7.15 | 56.4 | 71.6 | 64.8 | 21.8 | 19.8 | 1.4 | 2.8 |
| 3 | 550 | 1.80 | 1/0.5/2.4 | 88.9 | 87.8 | 73.8 | 0.18 | 0.15 | 3.7 | 6.3 |
| 4 | 550 | 1.20 | " | 96.8 | 83 | 66.7 | 0.26 | 0.17 | 7.1 | 11.4 |
| 5 | 500 | 1.92 | " | 97.9 | 70.5 | 53.0 | 0.15 | 0.12 | 23.9 | 35.9 |
| 6 | 550 | 2.4 | " | 97.4 | 87.3 | 74.4 | 0.13 | 0.11 | 6.4 | 10.8 |

*1,2-dichloroethane

What is claimed is:

1. A process for producing monohalogenated olefins which comprises reacting an alkane having 2 to 4 carbon atoms with a hydrogen halide and a source of oxygen at a temperature in the range from about 400° C. to about 650° C. in contact with a catalyst consisting essentially of a copper halide and an alkali metal phosphate, and optionally from about 0.1% to about 1% by weight of a platinum group metal, deposited upon an inorganic support.

2. The process of claim 1 wherein said inorganic support is alumina.

3. The process of claim 2 wherein said alkane is ethane and said hydrogen halide is hydrogen chloride.

4. A process of claim 3 wherein said copper halide is cupric chloride and said alkali metal phosphate is potassium phosphate.

5. The process of claim 4 wherein the concentration of copper on said support is from about 0.1 to about 10% by weight and the concentration of potassium as the phosphate is from about 1% to about 10% by weight.

6. The process of claim 5 wherein said catalyst has a surface area of $<10$ m$^2$/g.

7. The process of claim 6 wherein said temperature is in the range from about 500° to about 600° C.

8. The process of claim 7 wherein the relative molar proportions of alkane to hydrogen halide to oxygen are in the range from 1:0.25:0.5 to 1:2:5.

9. The process of claim 8 wherein said platinum-group metal is platinum.

10. The process of claim 9 wherein said catalyst also contains from about 0.5 to about 5.0% by weight of an alkali metal chloride.

* * * * *